US00PP36809P2

(12) United States Plant Patent
Smith

(10) Patent No.: US PP36,809 P2
(45) Date of Patent: Jul. 8, 2025

(54) ***CHRYSANTHEMUM* PLANT NAMED 'CIFZ0116'**

(50) Latin Name: ***Chrysanthemum* x *morifolium***
Varietal Denomination: CIFZ0116

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,472

(22) Filed: Jan. 31, 2025

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289, 295
CPC ..... A01H 5/0255
See application file for complete search history.

*Primary Examiner* — Kent L Bell
(74) *Attorney, Agent, or Firm* — Dale Skalla

(57) ABSTRACT

A new garden type *Chrysanthemum* plant named 'CIFZ0116' particularly distinguished by its medium size plant with round plant habit, medium to large size decorative flowers with yellow flower color and a natural season response late September/early October.

1 Drawing Sheet

Latin name of the genus and species of the plant claimed: *Chrysanthemum* x *morifolium.*

Varietal denomination: 'CIFZ0116'.

BACKGROUND OF THE NEW PLANT

The present invention comprises a new *Chrysanthemum*, botanically known as *Chrysanthemum* x *morifolium*, and hereinafter referred to by the variety name 'CIFZ0116'.

'CIFZ0116' is a product of a planned breeding program. The new cultivar has a medium size plant with round plant habit, medium to large size decorative flowers with yellow flower color and a natural season response late September/early October.

'CIFZ0116' originated from a mutation of X-ray treated cuttings in October 2021 in Fort Myers, Florida. 'CIFZ0116' was selected from the resulting plants on Mar. 25, 2022 in Alva, Florida.

The sport parent was an unnamed proprietary plant '03-M343-1GJ', a lavender decorative.

TABLE 1

Characteristics of the sport parent, compared to 'CIFZ0116':

| | 'CIFZ0116' | '03-M343-1GJ' |
|---|---|---|
| Natural response: | ½ week slower | ½ week faster |
| Blackcloth response: | Similar | Similar |
| Flower size: | Similar | Similar |
| Flower color: | Yellow | Lavender |
| Flower type: | Similar | Similar |
| Plant size: | Bit smaller | Bit larger |
| Plant habit: | Similar | Similar |
| Flowering uniformity: | Similar | Similar |

As the new variety is the result of mutation breeding, there is not a male parent.

The first act of asexual reproduction of 'CIFZ0116' was accomplished when vegetative cuttings were propagated from the initial selection in May 2022 in Alva, Florida.

BRIEF SUMMARY OF INVENTION

Horticultural examination of plants grown from cuttings of the plant initiated in May 2022 and continuing thereafter, has demonstrated that the combination of characteristics as herein disclosed for 'CIFZ0116' are firmly fixed and are retained through successive generations of asexual reproduction.

'CIFZ0116' has not been observed under all possible environmental conditions. The phenotype may vary significantly with variations in environment such as temperature, light intensity and day length.

A Plant Breeder's Right for this cultivar has not yet been applied for. 'CIFZ0116' has not been made publicly available prior to the effective filing date of this application, notwithstanding any disclosure that may have been made less than one year prior to the effective filing date of this application by the inventor or another who obtained 'CIFZ0116' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0116' with colors being as true as possible with an illustration of this type.

Figure 1:
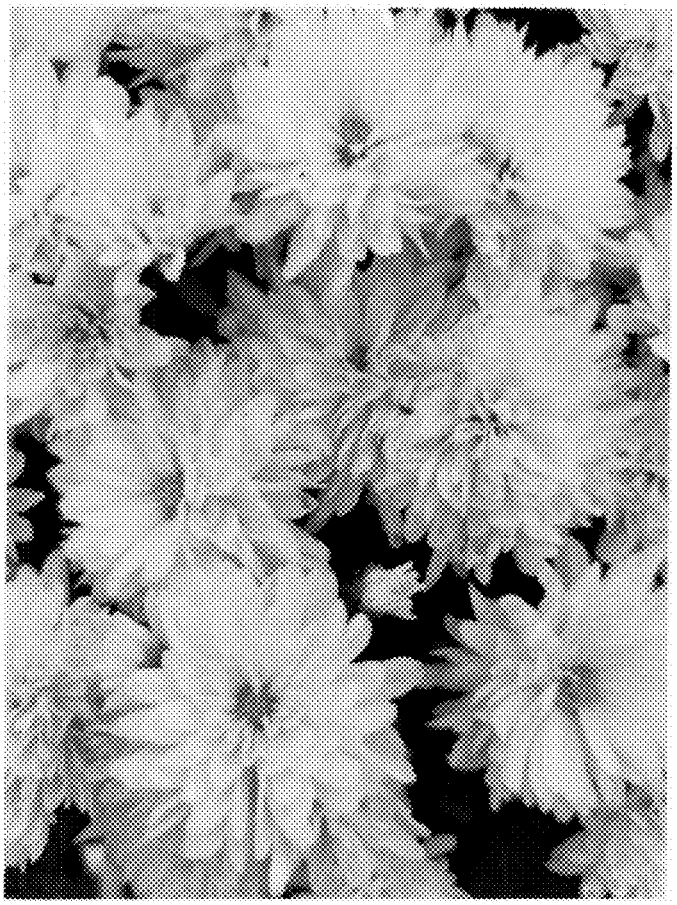
Figure 2:
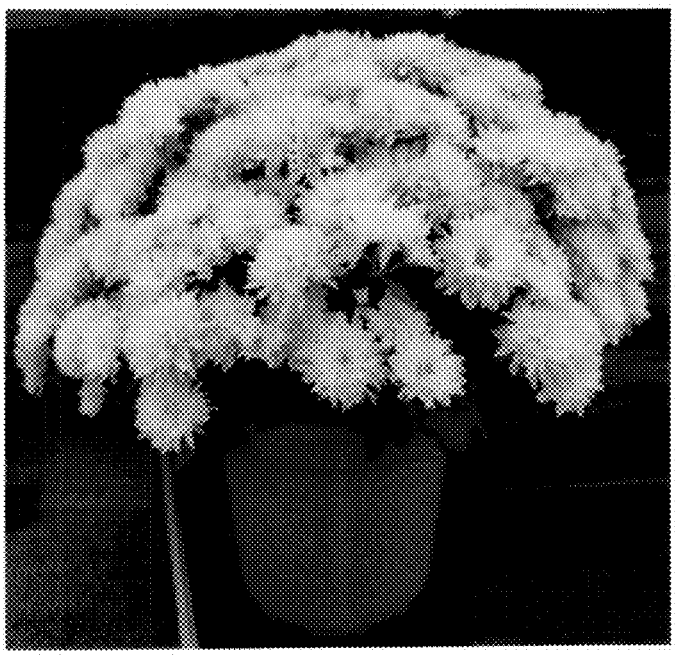

The photographic drawing shows in FIG. 1 a close view of flowers of the new variety and in FIG. 2 a flowering plant from an indoor trial.

The aforementioned photographs: FIG. 1, as well as FIG. 2, were taken on Sep. 2, 2024 both showing a plant from the same blackcloth outdoor trial in Andijk, The Netherlands.

These plants were about 13 weeks of age. One rooted cutting per pot had been planted in a 19 cm pot, not pinched in week 23, 2024 and black clothed from week 29. Plants started flowering the end of August 2024.

The measurements were taken in Andijk, The Netherlands in September 2024 on plants from the same outdoor black-cloth trial.

DETAILED BOTANICAL DESCRIPTION

Color references are made to The Royal Horticultural Society Colour Chart (R.H.S.) 2001.

TABLE 2

DIFFERENCES BETWEEN THE NEW VARIETY 'CIFZ0116' AND 'CIFZ0078':

| | 'CIFZ0116' | 'CIFZ0078', U.S. Plant Pat. No. 33,552 |
|---|---|---|
| Natural response: | Similar | Similar |
| Blackcloth response: | ½ week faster | ½ week slower |
| Flower size: | Larger | Smaller |
| Flower color: | Similar | Similar |
| Flower type: | Similar | Similar |
| Plant size: | Larger | Smaller |
| Plant habit: | Similar | Similar |
| Flowering uniformity: | Less uniform | More uniform |

TABLE 3

DIFFERENCES BETWEEN THE NEW VARIETY 'CIFZ0116' AND 'PPP CON Y05':

| | 'CIFZ0116' | 'PPP CON Y05', U.S. Plant Pat. No. 18,655 |
|---|---|---|
| Natural response: | Similar | Similar |
| Blackcloth response: | 1.5 weeks faster | 1.5 weeks slower |
| Flower size: | Bit smaller | Bit larger |
| Flower color: | Similar | Similar |
| Flower type: | Similar | Similar |
| Plant size: | Bit taller | Less height |
| Plant habit: | Similar | Similar |
| Flower longevity: | 20% longer lasting | 20% shorter life |

Plant:

*Form, growth and habit.*—Herbaceous garden-type, stems Upright and outwardly spreading, freely branching, strong and medium vigorous growth habit.

*Plant height (above soil).*—19 cm.

*Plant height (inflorescence included).*—24 cm.

*Plant width.*—33 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137B.

*Immature leaf, color lower surface.*—RHS 138A.

*Mature leaf, color, upper surface.*—RHS 137A.

*Mature leaf, color lower surface.*—RHS 137B.

*Length.*—6.0 cm.

*Width.*—3.5 cm.

*Shape.*—Ovate, with distinct lobes.

*Base shape.*—Attenuate.

*Apex shape.*—Apiculate.

*Margin.*—3 lobed.

*Number of margin indentations.*—2-3.

*Depth of margin indentations.*—1-2 mm.

*Leaf length terminal lobe relative to total leaf length.*—1:3.

*Leaf depth lower lateral sinus.*—1.0 cm.

*Texture, upper surface.*—Bifid hairs.

*Texture, lower surface.*—Bifid hairs.

*Color of veins, upper surface.*—RHS 138B.

*Color of veins, lower surface.*—RHS 139C.

*Pattern of veining.*—Palmate.

*Petiole color.*—No petiole present.

*Presence of stipules.*—No.

Stem:

*Quantity of main branches per plant.*—2-4.

*Color of stem.*—RHS 144A.

*Length of stem.*—9-12 cm.

*Diameter.*—0.3-0.4 cm.

*Length of internodes.*—1.0-4.0 cm.

*Texture.*—Bifid hairs.

*Color of peduncle.*—RHS 138B.

*Length of peduncle.*—1.5-4.0 cm.

*Peduncle diameter.*—0.2 cm.

*Texture.*—Bifid hairs.

Inflorescence:

*Type.*—Compositae, solitary, decorative inflorescences borne terminally above foliage, ligulate ray florets arranged in whorls on a capitulum giving a double flower.

*Quantity of short days to flowering (response time).*—Approximately 6.5 weeks.

*Quantity of inflorescences per plant.*—About 240 with some small buds developing.

*Lastingness of individual blooms on the plant.*—About six weeks from first color.

*Fragrance.*—Slightly spicy.

Bud (when showing color):

*Color.*—RHS 8B.

*Length.*—0.9 cm.

*Width.*—0.7 cm.

*Shape.*—Oblate.

Immature inflorescence (at moment of opening):

*Diameter.*—1.4 cm.

*Color of ray florets, upper surface.*—RHS 9A.

*Color of ray florets, lower surface.*—RHS 8A.

Mature inflorescence:

*Diameter.*—3.5 cm.

*Depth.*—1.5 cm.

*Total diameter of disc.*—0.4 cm.

*Receptacle color.*—RHS 138A.

*Receptacle height.*—0.4 cm.

*Receptacle diameter.*—1.2 cm.

*Length of corolla tube.*—0 cm.

Ray florets:

*Average quantity of florets.*—140.

*Number of whorls per inflorescence.*—17-19.

*Color of florets, upper surface.*—RHS 12B.

*Color lower surface.*—RHS 10A.

*Length.*—1.5 cm.

*Width/diameter.*—0.3 cm.

*Shape.*—Oblong.

*Apex shape.*—Acute.

*Base shape.*—Shortly attenuate.

*Margin*.—Entire. Small incisions may be present at tip.
*Margin: type of rolling*.—Moderately revolute.
*Texture, upper surface*.—Papillate.
*Lower surface*.—Papillate.
*Ribs present*.—No.
*Number of keels*.—0-1.
*Profile at widest point*.—Moderately convex.
*Longitudinal axis shape*.—Moderately incurving.
*Longitudinal axis curvature strength*.—Moderate.
*Corolla tube shape*.—No tube.

Disc florets:
*Number of disc florets*.—20-50.
*Width*.—0.1 cm.
*Length*.—0.3 cm.
*Color*.—Base RHS 158D, top RHS 12A.

Inflorescence (at moment of senescence):
*Color of ray florets, upper surface*.—RHS 12A.
*Color of ray florets, lower surface*.—RHS 11A.

Phyllaries:
*Quantity*.—28.
*Color, upper surface*.—RHS 138A.
*Color, lower surface*.—RHS 137B.
*Length*.—0.6 cm.
*Width*.—0.2 cm.
*Shape*.—Ensiform.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—Fully developed female organs not found, occasionally rudimentary pistils found in a few disc florets, maximum one per disc floret.
*Length*.—0-0.3 cm.
*Style color*.—RHS 130D.
*Style length*.—0.2 cm.
*Stigma color*.—No stigmas observed.
*Stigma shape*.—No stigmas observed.
*Ovary color*.—RHS 145D.
*Ovary length*.—0.2 cm.
*Ovary width*.—0.1 cm.

Androecium:
*Stamens*.—0-1, found occasionally, on only disc florets.
*Color of filaments*.—RHS 157D.
*Length filaments*.—0.2 cm.
*Anther color*.—RHS 1B.
*Anther length*.—0.1 cm.
*Anther shape*.—Irregular shaped.
*Color of pollen*.—No pollen observed.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0116' substantially as illustrated and described herein.

* * * * *